(12) United States Patent
Wedan et al.

(10) Patent No.: US 9,271,664 B2
(45) Date of Patent: *Mar. 1, 2016

(54) COMBINED FIELD LOCATION AND MRI TRACKING

(75) Inventors: Steven R. Wedan, Savage, MN (US); Thomas W. Lloyd, Eagan, MN (US); Gregg S. Stenzel, Victoria, MN (US)

(73) Assignee: IMRICOR MEDICAL SYSTEMS, INC., Burnsville, MN (US)

(*) Notice: Subject to any disclaimer, the term of this patent is extended or adjusted under 35 U.S.C. 154(b) by 1154 days.

This patent is subject to a terminal disclaimer.

(21) Appl. No.: 13/202,705

(22) PCT Filed: Mar. 4, 2010

(86) PCT No.: PCT/US2010/026227
§ 371 (c)(1),
(2), (4) Date: Aug. 22, 2011

(87) PCT Pub. No.: WO2010/102119
PCT Pub. Date: Sep. 10, 2010

(65) Prior Publication Data
US 2011/0306872 A1    Dec. 15, 2011

Related U.S. Application Data

(60) Provisional application No. 61/157,484, filed on Mar. 4, 2009.

(51) Int. Cl.
*A61B 5/06* (2006.01)
*A61B 19/00* (2006.01)
*G01R 33/28* (2006.01)
*A61B 5/055* (2006.01)

(52) U.S. Cl.
CPC .............. *A61B 5/062* (2013.01); *A61B 5/055* (2013.01); *A61B 19/52* (2013.01); *A61B 19/5244* (2013.01); *G01R 33/287* (2013.01); *A61B 2019/5236* (2013.01); *A61B 2019/5251* (2013.01); *A61B 2019/5289* (2013.01)

(58) Field of Classification Search
CPC .......... A61B 5/06; A61B 5/062; A61B 5/063; A61B 5/065; A61B 2019/5251; A61B 2019/5272; A61B 2019/5454; A61B 19/5244
See application file for complete search history.

(56) References Cited

U.S. PATENT DOCUMENTS

| 4,647,972 | A | 3/1987 | Strehl |
| 6,035,226 | A | 3/2000 | Panescu |
| 8,271,069 | B2 * | 9/2012 | Jascob et al. ................. 600/424 |
| 2001/0021805 | A1 * | 9/2001 | Blume et al. ................. 600/407 |
| 2002/0058868 | A1 | 5/2002 | Hoshino et al. |
| 2002/0077546 | A1 * | 6/2002 | Aldefeld et al. .............. 600/424 |

(Continued)

*Primary Examiner* — Amanda Lauritzen Moher
(74) *Attorney, Agent, or Firm* — Barbara A. Wrigley; Fox Rothschild LLP

(57) ABSTRACT

A composite tracking system for a medical device comprises a field location tracking system including at least one field location sensor structured to be coupled to a medical device, a magnetic resonance tracking system including at least one tracking coil structured to be coupled to a medical device, and a composite tracking processor operably coupled to the field location tracking system and the magnetic resonance tracking system. The composite tracking processor is operable to receive and process field location parameters from the field location tracking system and positional coordinates from the magnetic resonance tracking system to register a field location coordinate system to a magnetic resonance coordinate system.

4 Claims, 9 Drawing Sheets

(56) References Cited

U.S. PATENT DOCUMENTS

| | | | |
|---|---|---|---|
| 2002/0173714 A1* | 11/2002 | Tsukada et al. | 600/409 |
| 2002/0198448 A1 | 12/2002 | Zuk et al. | |
| 2003/0050557 A1 | 3/2003 | Susil et al. | |
| 2003/0055317 A1* | 3/2003 | Taniguchi et al. | 600/117 |
| 2003/0065260 A1 | 4/2003 | Cheng et al. | |
| 2003/0216639 A1* | 11/2003 | Gilboa et al. | 600/424 |
| 2004/0097803 A1* | 5/2004 | Panescu | 600/424 |
| 2004/0186681 A1 | 9/2004 | Harle | |
| 2004/0258329 A1 | 12/2004 | Jiang et al. | |
| 2005/0054910 A1* | 3/2005 | Tremblay et al. | 600/411 |
| 2005/0245814 A1 | 11/2005 | Anderson et al. | |
| 2006/0084867 A1 | 4/2006 | Tremblay et al. | |
| 2007/0288058 A1 | 12/2007 | Halperin et al. | |
| 2007/0299351 A1 | 12/2007 | Harlev et al. | |
| 2008/0118103 A1* | 5/2008 | Pescatore et al. | 382/103 |
| 2008/0119919 A1 | 5/2008 | Atalar et al. | |
| 2008/0243218 A1 | 10/2008 | Bottomley et al. | |
| 2009/0171421 A1 | 7/2009 | Atalar et al. | |
| 2010/0114276 A1 | 5/2010 | Min et al. | |
| 2011/0105897 A1* | 5/2011 | Kornblau et al. | 600/436 |

* cited by examiner

| (Px, X) COORDINATES | (Py, y) COORDINATES | (Pz, Z) COORDINATES |
|---|---|---|
| (Px1, X1) | (Py1, y1) | (Pz1, Z1) |
| (Px2, X2) | (Py2, y2) | (Pz2, Z2) |
| (Px3, X3) | (Py3, y3) | (Pz3, Z3) |
| (Px4, X4) | (Py4, y4) | (Pz4, Z4) |
| (Px5, X5) | (Py5, y5) | (Pz5, Z5) |
| (Px6, X6) | (Py6, y6) | (Pz6, Z6) |
| ... | ... | ... |
| (PxN, XN) | (PyN, yN) | (PzN, ZN) |

Fig. 4

| $(P_x, X, P_y, Y, P_z, Z)$ COORDINATES |
|---|
| $(P_{x1}, X_1, P_{y1}, Y_1, P_{z1}, Z_1)$ |
| $(P_{x2}, X_2, P_{y2}, Y_2, P_{z2}, Z_2)$ |
| $(P_{x3}, X_3, P_{y3}, Y_3, P_{z3}, Z_3)$ |
| $(P_{x4}, X_4, P_{y4}, Y_4, P_{z4}, Z_4)$ |
| $(P_{x5}, X_5, P_{y5}, Y_5, P_{z5}, Z_5)$ |
| $(P_{x6}, X_6, P_{y6}, Y_6, P_{z6}, Z_6)$ |
| ... |
| $(P_{xN}, X_N, P_{yN}, Y_N, P_{zN}, Z_N)$ |

Fig. 9

COMBINED FIELD LOCATION AND MRI TRACKING

FIELD OF THE INVENTION

The invention relates to the tracking of medical devices used in diagnostic and therapeutic procedures and in particular to a system and method for combining field location tracking with magnetic resonance imaging tracking of a medical device.

BACKGROUND OF THE INVENTION

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

MRI uses three fields to image patient anatomy: a large static magnetic field, a time-varying magnetic gradient field, and a radiofrequency (RF) electromagnetic field. The static magnetic field and time-varying magnetic gradient field work in concert to establish both proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

For imaging of soft tissue of patients with implanted medical devices, such as catheters, guidewires, stents, cardiac defibrillators (ICDs), pacemakers, neurostimulators, cochlear implants, and the like, MRI is preferable to other modalities including X-ray, computer tomography, ultrasound and positron emission tomography (PET).

Localization of medical devices during use is desirable and often required for medical procedures. For example, as a medical device is advanced through the patient's body during an interventional procedure, its progress may be tracked so that the device can be delivered properly to a target site. Once delivered to the target site, the device can be monitored to determine whether it has been placed properly and/or is functioning properly. Providing the ability to track the location of medical devices is useful in interventional procedures such as cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the location of medical devices using MRI is also useful in oncological procedures such as breast, liver and prostate tumor ablations; and urological procedures such as uterine fibroid and enlarged prostate ablations.

Currently, several methods of locating position(s) of a medical device during a medical procedure exist. One exemplary method is a magnetic field method. In this method, a magnetic field is transmitted that permeates all non-metallic surfaces. A miniaturized sensor designed for medical applications is placed on the instrument that is inserted into the body. The location of the sensor may be determined based upon magnetic field strength and/or orientation. Another exemplary method is an impedance based method. In this method, an electric field is transmitted through the body and the bioimpedance is measured between locations. The location of a medical device or instrument may then be determined based upon the impedance variance. Another exemplary method utilizes an ultrasound transducer to provide an image of a medical device and procedural tissue used in positioning. Yet another exemplary method uses optical trackers that emit or reflect a light source that is in turn sensed by one or more detectors. The light source is typically infrared, but may alternatively operate in another frequency range as will be appreciated by those skilled in the art.

This non-exhaustive list of exemplary methods may be termed "field location" techniques. Each of these field location techniques provides spatial coordinates (i.e. x, y, z) relative to a point external to the patient. The spatial coordinates are provided in what is commonly referred to as "absolute" space. As appreciated by those skilled in the art, providing spatial coordinates in absolute space requires registration of the external point relative to the patient. Thus, one disadvantage of such field location techniques arises from the fact that if the position of the patient changes during a procedure, re-registration with respect to the external reference location is required. Another disadvantage of field location techniques is their inherent accuracy limitations due to non-ideal and/or non-homogeneous field behavior in the body.

In an attempt to overcome the disadvantages inherent in field location techniques, it is possible to utilize the MR scanner to determine the location of a tracking coil embedded in or attached to the medical device or instrument. Thus, tracking position using the MR scanner is an alternative to using field location techniques such as those previously described. MR tracking has the advantage of requiring no registration with respect to any external point or reference images generated by the MRI, as images created with MRI are referenced to so-called "patient" space. However, when MM is utilized for both tracking and imaging, there may be a decrease in the imaging performance because tracking sequences must be time multiplexed with imaging sequences.

When used in combination with MRI, field location techniques will suffer from being referenced to absolute space rather than patient space. Patient space is a coordinate system that includes spatial warping caused by non-ideal gradient fields. For instance, assume that at some absolute point $(x=y=z=0)$, patient and absolute space may be perfectly aligned. However, as one moves away from that point, patient space may be nonlinear or increase with a different scale as compared to absolute space. As such, circular objects imaged with MRI may appear somewhat oblong. Correction software in the MRI may be used to compensate for this effect. Such compensation is, in general, dynamic, in that different compensation is required for different images, depending upon several variables. In addition, absolute space may be offset from patent space such that registration of the two spaces is required (for example, $(x=y=z=0)$ for absolute space may not be $(x=y=z=0)$ for patient space, and/or the two spaces may be rotated with respect to one another.

As will be understood based on the foregoing, current technologies for tracking a medical device are inadequate. Thus, what is needed is a system and method that combines the benefits of both field location and MRI techniques to provide an improved means for locating and tracking a medical device.

BRIEF SUMMARY OF THE INVENTION

The present invention solves the foregoing needs by providing a composite tracking system for a medical device that includes a field location tracking system having at least one field location sensor structured to be coupled to a medical device, a magnetic resonance tracking system having at least one tracking coil structured to be coupled to a medical device, and a composite tracking processor operably coupled to the field location tracking system and the magnetic resonance tracking system. The composite tracking processor is operable to receive and process field location parameters from the field location tracking system and positional coordinates from the magnetic resonance tracking system to register a field location coordinate system to a magnetic resonance coordinate system.

In accordance with another aspect of the present invention, a method of calibrating field location tracking to magnetic resonance tracking is provided that generally includes the steps of moving a medical device throughout a plurality of points within a patient volume, tracking the medical device with a field location tracking system and a magnetic resonance tracking system, calculating a plurality of magnetic resonance tracking locations, determining a plurality of field location parameters that correspond to the plurality of magnetic resonance tracking locations, and creating a transfer function that maps the field location parameters to the magnetic resonance tracking locations, wherein the transfer function registers a field location coordinate system to a magnetic resonance coordinate system.

BRIEF DESCRIPTION OF THE DRAWINGS

FIG. 4 is a table showing a plurality of recorded data sets in monotonically increasing order.

FIG. 9 is a table showing an exemplary multidimensional coordinate set that may be used in accordance with one alternative method of the present invention.

DETAILED DESCRIPTION OF THE INVENTION

Figure 1:
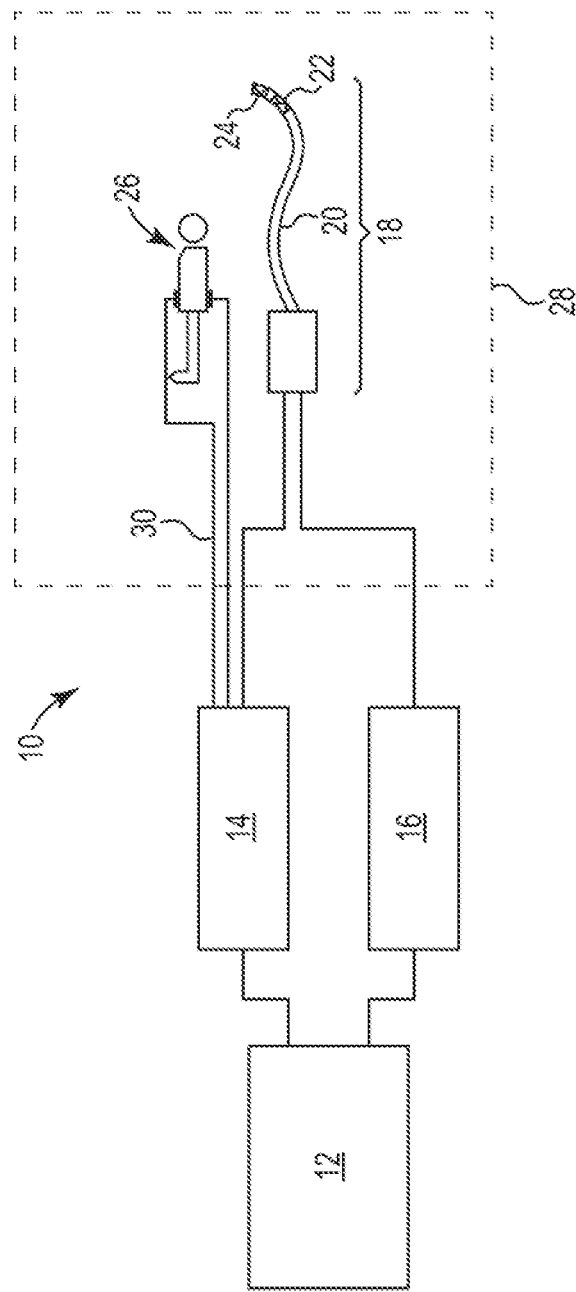
FIG. 1 is a diagram illustrating one exemplary embodiment of a composite tracking system in accordance with the present invention.

The present invention is a system and method for combining field location techniques with MRI tracking to provide an improved means for locating and tracking the position of a medical device. Generally speaking, both MRI tracking and field location are performed simultaneously to collect position or location data. The MRI tracking location is then used to calibrate and register the field location, effectively compensating for gradient warping effects and minimizing the field location inaccuracies. The calibration may be performed with software, and may be accomplished with or without user input. Once this calibration is performed, the MRI tracking may be turned off and the field location may be used to locate and track the medical device in patient space while retaining the accuracy benefits provided by MRI tracking. During a medical procedure using this technique, periodic calibration sequences may be performed to ensure that the field location does not lose registration or calibration.

MR tracking is a well-known technique wherein an MR tracking coil is embedded in a medical device such that the location of the MR tracking coil may be determined. This is typically accomplished by applying a pulse sequence in which only one of the three gradients is applied at a given time, and MR k-space data is recorded from the signal received by the MR tracking coil. By calculating the Fourier Transform of each of the three received k-space signals, the location of the MR tracking coil in each of the gradient directions may be determined (i.e. x-, y-, and z-directions).

A key advantage of MR tracking when used with MR imaging is that the location of the MR tracking coil is relative to "patient" space. Patient space is an image space which may be distorted from real or "absolute" space. Since the distortion or warping of a given MR image will give rise to an identical distortion or warping of the MR tracking location, the two are matched and the MR tracking coil location can be precisely determined relative to the tissue in which it resides. For example, if a circular object is scanned with MRI and the resultant image is an oval, guiding an MR tracking coil around the circumference of the circle and tracking its location would result in the recorded location points also defining an oval shape. However, whether the resultant image (i.e. an oval) accurately represents the actual shape (i.e. a circle) is irrelevant. It is only important that the relative location of the tracking coil to the circle is consistent and repeatable. One drawback to MR tracking is that the tracking sequences must be interweaved between imaging sequences. As a result, imaging speed performance may suffer. This may be particularly problematic when imaging in real time or near real time, where fast image formation and frame rates are desirable.

As previously discussed, numerous field location techniques exist including, but not limited to, impedance based field location, magnetic field location, electromagnetic field location, optical field location, and ultrasonic field location. Each of these techniques involves the measurement of a different electromagnetic or mechanical field parameter such as impedance, voltage, current, time delay, sound intensity, or the like. Regardless of the type of field parameter measured, each of the various field location techniques may be used to determine positional locations in absolute space. By way of example, consider basic impedance based field location. For this technique, three sets of external electrode patches are typically placed on the patient in predetermined locations. A first set of patches creates an electric field in the x-direction, a second set of patches creates an electric field in the y-direction, and a third set of patches creates an electric field in the z-direction. Voltage measured by the field location system at a sensor on the medical device, such as an electrode in the case of an impedance based system, may be used to determine the location of the device in each of the three dimensions, one at a time. The three measurements may be acquired quickly enough to be considered coincident in time for all practical purposes.

The error associated with field location technologies varies, and processes have been developed in an attempt to minimize the error. These processes are specific to the various field location technologies, and the applicable process therefore depends upon the technique that is being used. One major drawback is that field location techniques estimate the location of a device in absolute space, which may not correspond well to patient space, as described above. Additionally, non-homogenous characteristics of patient tissue produce errors in many field location techniques.

This invention broadly combines field location techniques with MR tracking such that the key advantage of MR tracking, i.e. precise location of the MR tracking coil relative to tissue, can be used to calibrate a field location technique. This allows the field location technique to precisely locate a medical device in the patient with similar performance to MR tracking, but without having to interrupt MR imaging pulse sequences to run MR tracking pulse sequences. Thus, the present invention combines the "accuracy" benefits of MR tracking with the "time performance" benefits of field location techniques.

FIG. 1 is a diagram illustrating one exemplary composite tracking system 10 in accordance with the present invention. As illustrated in FIG. 1, the composite tracking system 10 generally includes a composite tracking processor 12, a field location system 14, and a MR tracking system 16. The field location system 14 and the MR tracking system 16 are operably coupled to the composite tracking processor 12 to provide field location and MR tracking information, respectively, to the composite tracking processor 12 for processing. The composite tracking system 10 further includes a medical device 18 such as a catheter having a body 20 with at least one field location sensor 22 and at least one MR tracking coil 24. The medical device 18 is represented generically herein as a catheter merely for purposes of example and not limitation. However, the system and method of the present invention may be utilized with any type of medical device that necessitates tracking as will be appreciated by those skilled in the art.

Although the field location sensor 22 and the MR tracking coil 24 may be offset from one another, they are preferably in close proximity, such as separated by an offset distance of less than about 5 mm in one exemplary embodiment. As will be appreciated by those skilled in the art, if the field location sensor 22 and the MR tracking coil 24 are separated by a large distance and the portion of the medical device upon which they are attached experiences bending or deformation, the relative distance between the two elements may change significantly which could in turn impact the accuracy of the calibration process. In alternative embodiments where multiple field location sensors 22 and/or MR tracking coils 24 are utilized, the need for the sensors and/or tracking coils to be in close proximity may be eliminated, as long as the distance between the field location sensors and the MR tracking coils is both fixed and known.

As further illustrated in FIG. 1, a patient 26 is positioned within an MR scanner 28. A plurality of field location sources/receivers 30 are positioned external to the patient 26. In one exemplary embodiment, the field location sources/receivers 30 may comprise electrode patches as described above for the example of impedance based field location. Particularly, three sets of field location sources/receivers 30 would be placed on the patient in predetermined locations to create an electric field in each of the x-, y-, and z-directions. The structure, function, and number of the field location sources/receivers 30 will be dependent upon the class of field location technology being used. Thus, impedance based techniques are described herein merely for purposes of example and not limitation.

The field location system 14 is positioned outside of the MR scanner 28, and is operably coupled to the external field location sources/receivers 30 as well as to the field location sensor 22 on the medical device 18. The MR tracking system 16 is operably coupled to the MR tracking coil 24 on the medical device 18. The MR tracking system 16 may be structured as part of the MR scanner 28, but may also include an external MR processor for determining the location of the MR tracking coil 24 based on raw k-space data received from the MR scanner 28. The composite tracking processor 12 is operably coupled so as to receive MR tracking coil location data from the MR tracking system 16 and parameter data from the field location system 14. Once again, the nature of the parameter data will vary depending on the class of field location technique being used, but may comprise voltage, impedance, current, time delay, sound intensity, or the like. With regard to impedance base field location, for example, the field location system 14 may measure voltages at the field location sensor 22 on the medical device 18, which may be processed by the field location system 14 or the composite tracking processor 12 to determine the positional coordinates of the device in the x-, y-, and z-directions.

Figure 2:
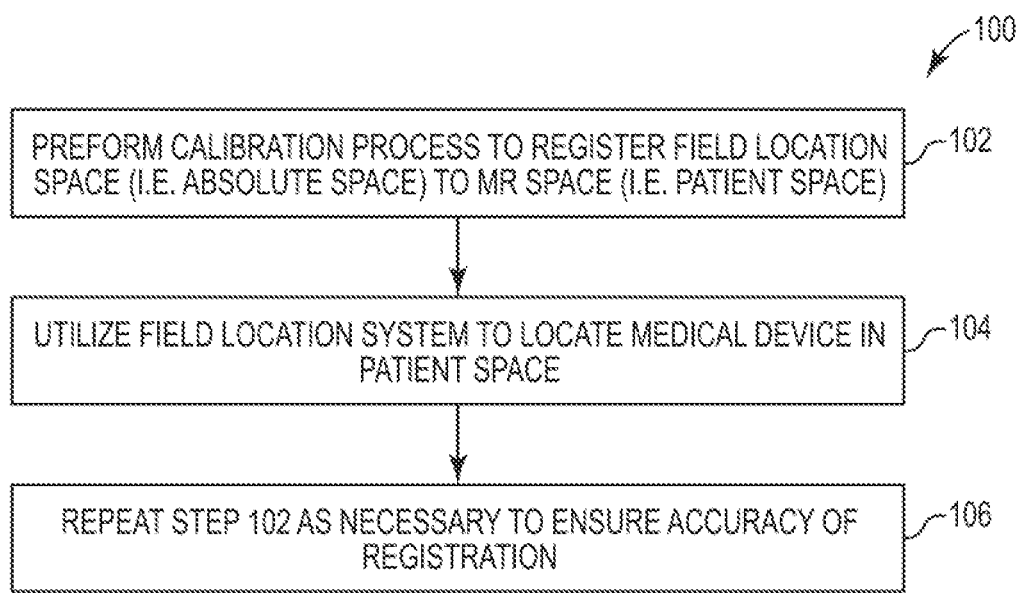
FIG. 2 is a flow diagram broadly illustrating an exemplary composite tracking method in accordance with the present invention.

Now that one exemplary embodiment of a composite tracking system has been described, an exemplary method of operating the composite tracking system to allow a field location system to precisely locate a medical device in patient space with similar performance to MR tracking will be described. The exemplary method of the present invention may generally be separated into two processes, including a calibration process 200 and a locating process 300. FIG. 2 is a flow diagram broadly illustrating the exemplary method 100 of the present invention. The calibration process 200 and the locating process 300 are described in greater detail with reference to FIGS. 3-9.

As illustrated in FIG. 2, the exemplary method 100 begins at step 102 with the calibration process 200. The calibration process 200 is operable to register field location space (i.e. absolute space) to MR space (i.e. patient space). Once the calibration process is complete and field location space is registered to MR space, the method 100 continues at step 104 where MR tracking is discontinued and field location may be used to locate a medical device in MR space. Optionally, at step 106, the calibration process 200 may be repeated periodically to ensure that the field location space does not lose registration with the MR space.

Figure 3:
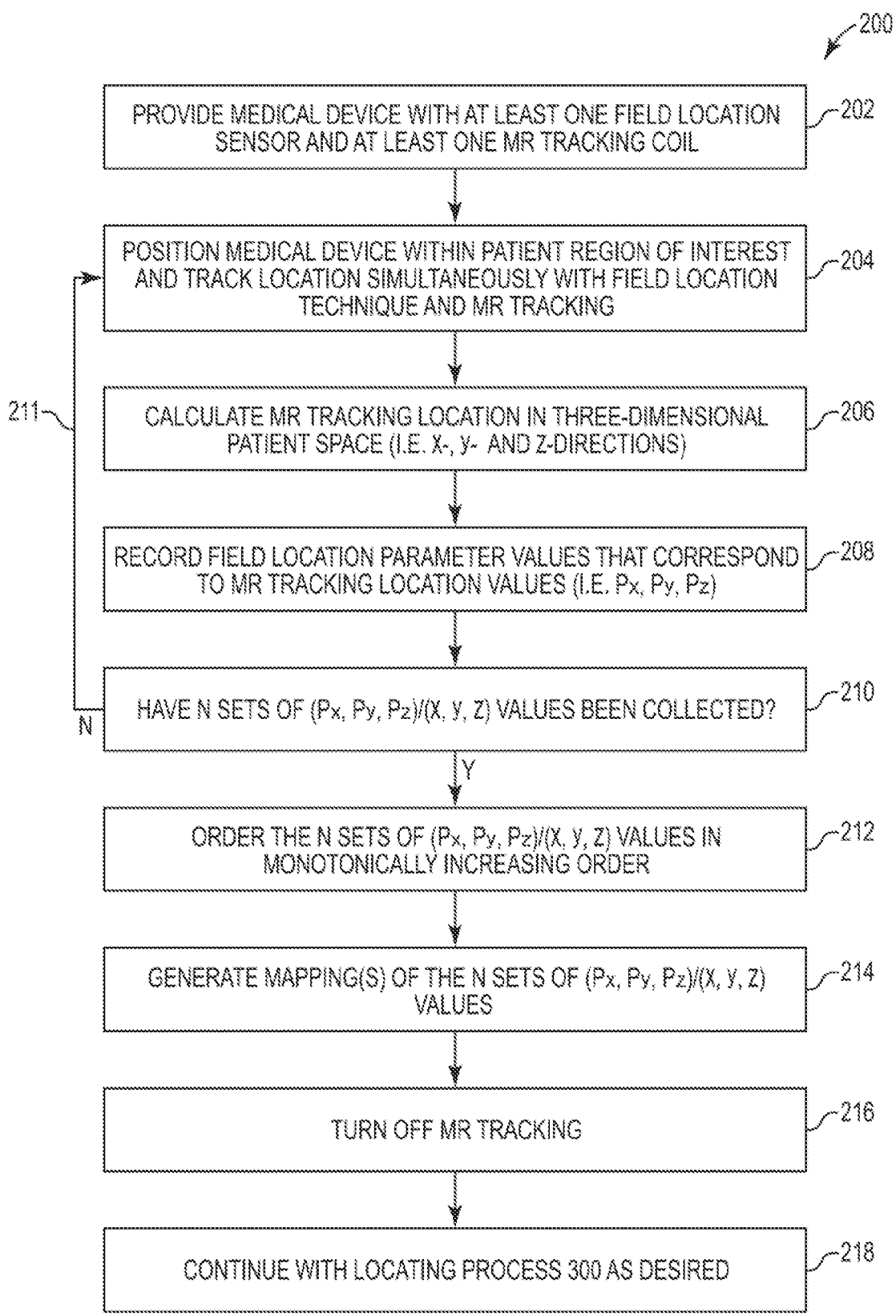
FIG. 3 is a flow diagram illustrating exemplary steps in a calibration process in accordance with one embodiment of the present invention.

FIG. 3 is a flow diagram illustrating exemplary steps in the calibration process 200 in accordance with one embodiment of the present invention. Beginning with step 202, a medical device is provided having at least one field location sensor and at least one MR tracking coil operably coupled thereto. The medical device may be any type of medical device that necessitates tracking. The structure and function of the field location sensor will depend upon the field parameter being measured, such as voltage, impedance, current, time delay, sound intensity, or the like.

The process continues at step 204 where the medical device is positioned within the region of interest in the patient. This region corresponds to the range of locations wherein the medical device will later be tracked by field location alone. As the medical device is being positioned within the region of interest, the location of the medical device is tracked simultaneously with the field location system and the MR tracking system. Next, in step 206, an MR tracking location in three-dimensional space is calculated. The MR tracking location includes an x-location value, a y-location value, and a z-location value that together provide the three-dimensional location of the MR tracking coil at that particular instant in time. The field location parameter values that correspond to the MR tracking location values are simultaneously recorded in step 208. Thus, the recorded data set will include an x-location parameter value, a y-location parameter value, and a z-location parameter value.

Once the three-dimensional MR tracking location in patient space is calculated and the corresponding field location parameter values recorded, the process continues at step 210 wherein the system will determine whether the requisite number of sets N of field location parameter values ($p_x$, $p_y$, $p_z$) and MR tracking location values (x, y, z) have been collected. As will be appreciated by those skilled in the art, the number of data sets N that must be collected may be any number greater than or equal to two, and may depend upon the tissue volume or range in which tracking is needed. As will be appreciated by those skilled in the art, two data sets will provide only a linear mapping. Thus, a larger number of data sets may be used in order to generate a polynomial mapping, which will improve the precision of the calibration process. The data sets may preferably include points along the outer boundary of the patient volume as well as points within the boundary.

If the system determines that the requisite number of data sets N has not been collected, the process 200 enters a loop 211 where steps 204-208 are repeated for additional positions of the medical device within the patient region of interest. Once the system determines that the requisite number of data sets N has been collected, this portion of the process is complete and the process moves on to step 212

Figure 5:
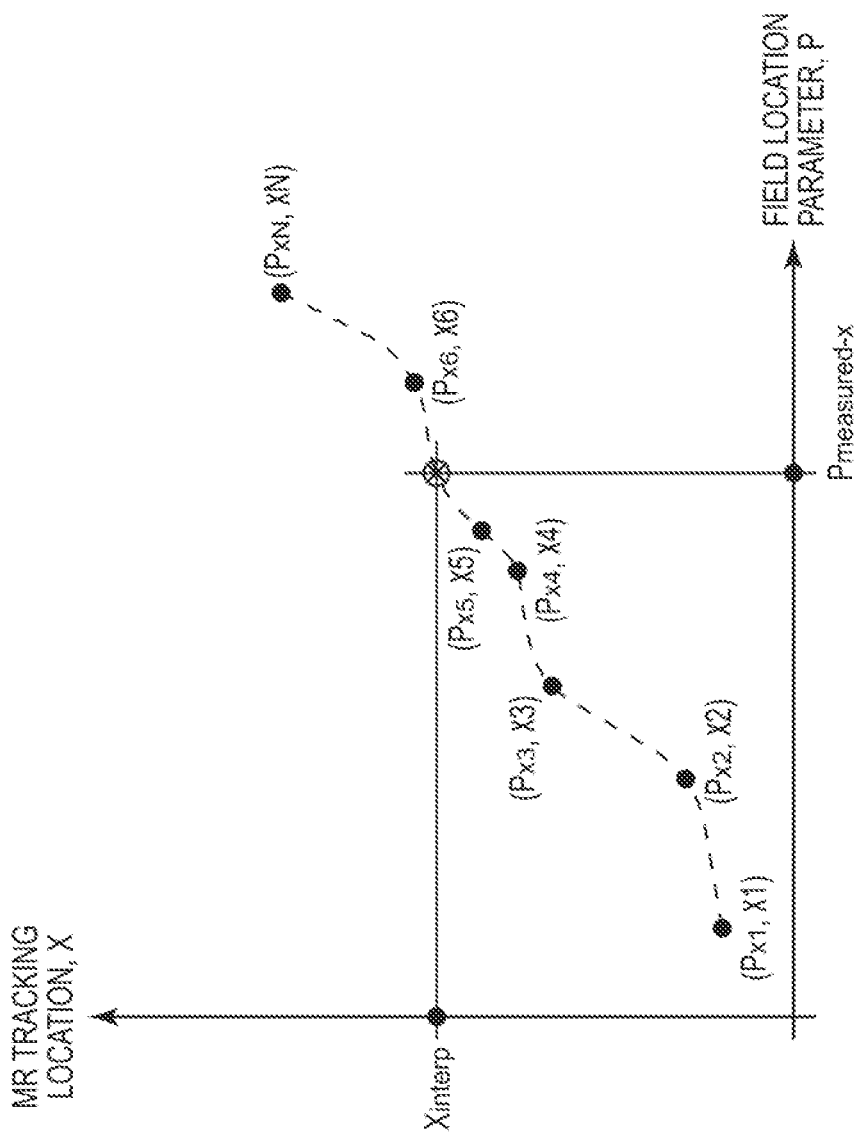
FIG. 5 is a graph illustrating an exemplary mapping of calculated x-location values in patient space and corresponding field location parameter values.
Figure 6:
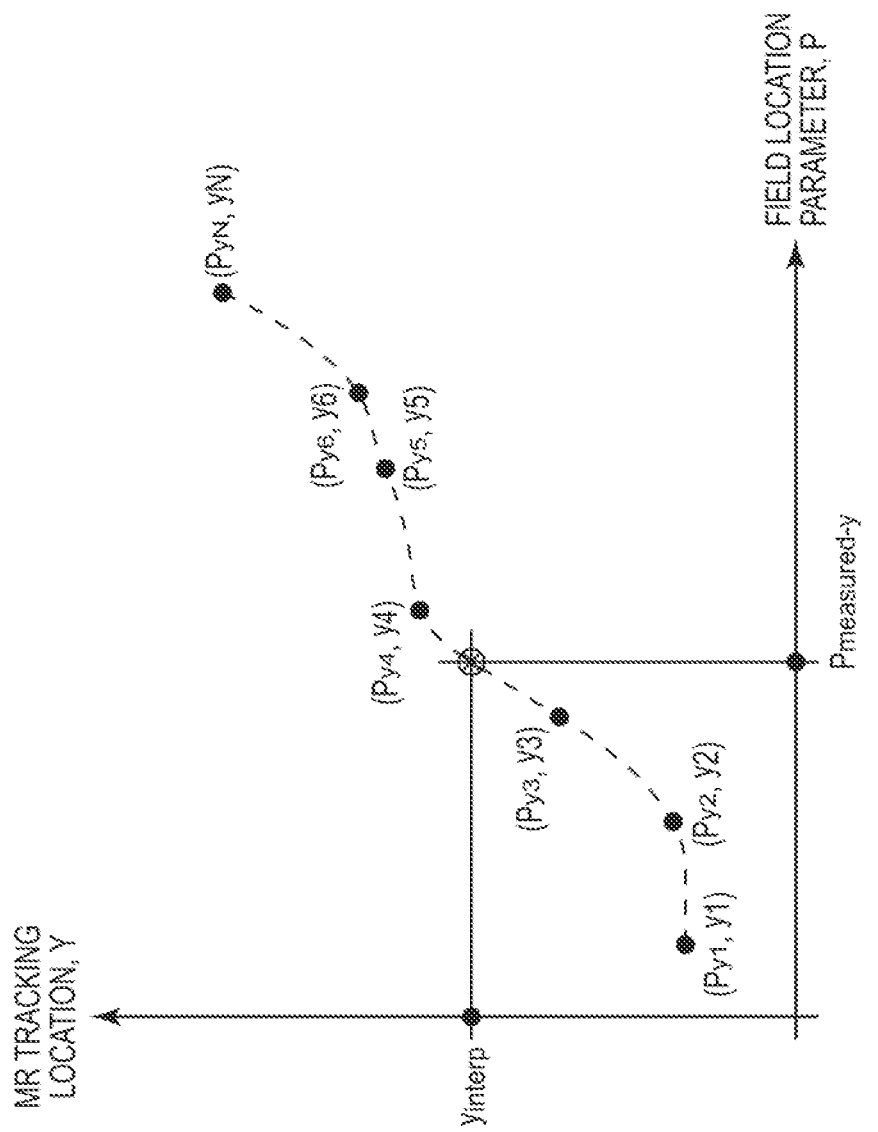
FIG. 6 is a graph illustrating an exemplary mapping of calculated y-location values in patient space and corresponding field location parameter values.
Figure 7:
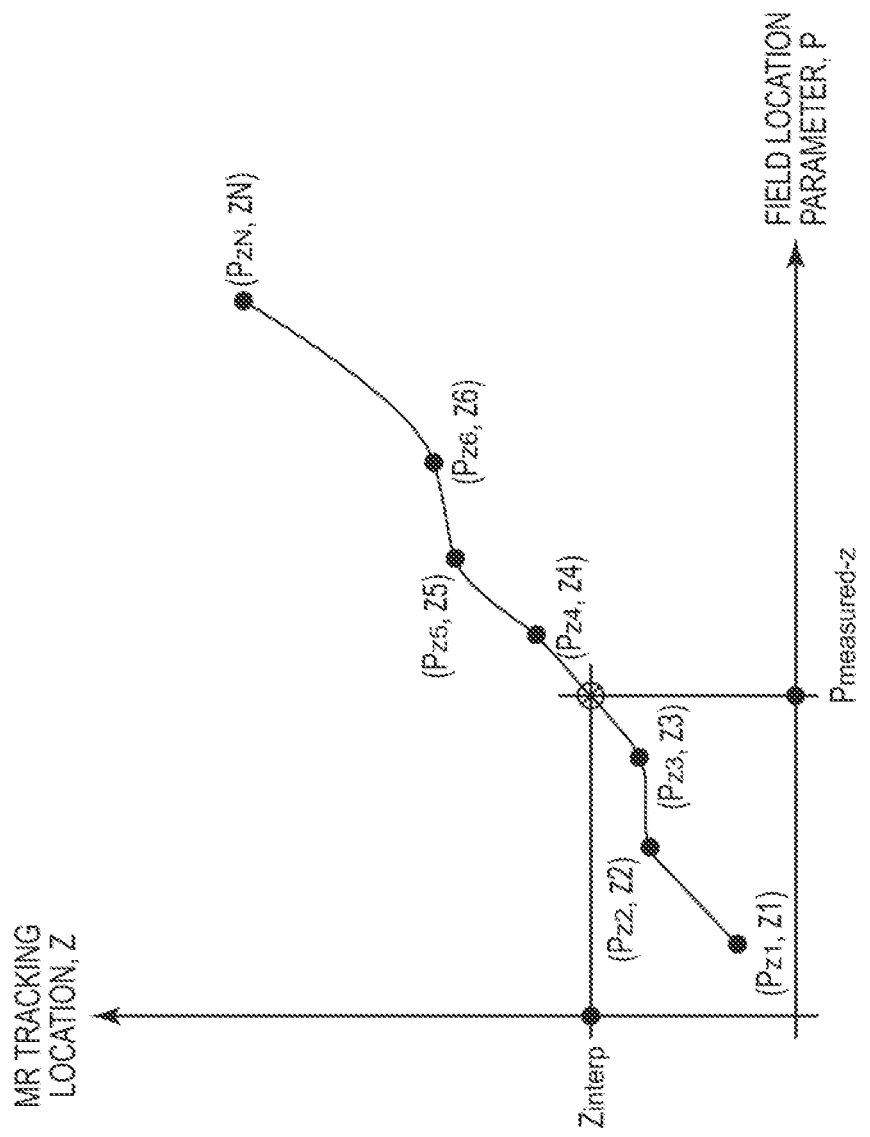
FIG. 7 is a graph illustrating an exemplary mapping of calculated z-location values in patient space and corresponding field location parameter values.

In step 212, the N data sets of ($p_x$, $p_y$, $p_z$)/(x, y, z) values are ordered in monotonically increasing order and stored in memory. This process is illustrated in the table shown in FIG. 4. After ordering the data sets in step 212, the process continues at step 214 where mappings of the N data sets are generated. In one exemplary embodiment, three separate mappings may be generated including a ($p_x$, x) mapping as illustrated in FIG. 5, a ($p_y$, y) mapping as illustrated in FIG. 6, and a ($p_z$, z) mapping as illustrated in FIG. 7. These "mappings" represent transfer functions that may be used during field location tracking to map a measured field location parameter value to an observed point in patient space as will be discussed in further detail to follow. It is important to note that the ($p_x$, x), ($p_y$, y), and ($p_z$, z) coordinates do not need to be uniformly distributed along either of the axes.

Once the x-, y-, and z-location mappings are generated, the MR tracking may be discontinued in step 216. The calibration process is now complete, and field location space (i.e. absolute space) is registered to MR space (i.e. patient space). The surgeon may continue with the locating process 300 as indicated at step 218.

Figure 8:
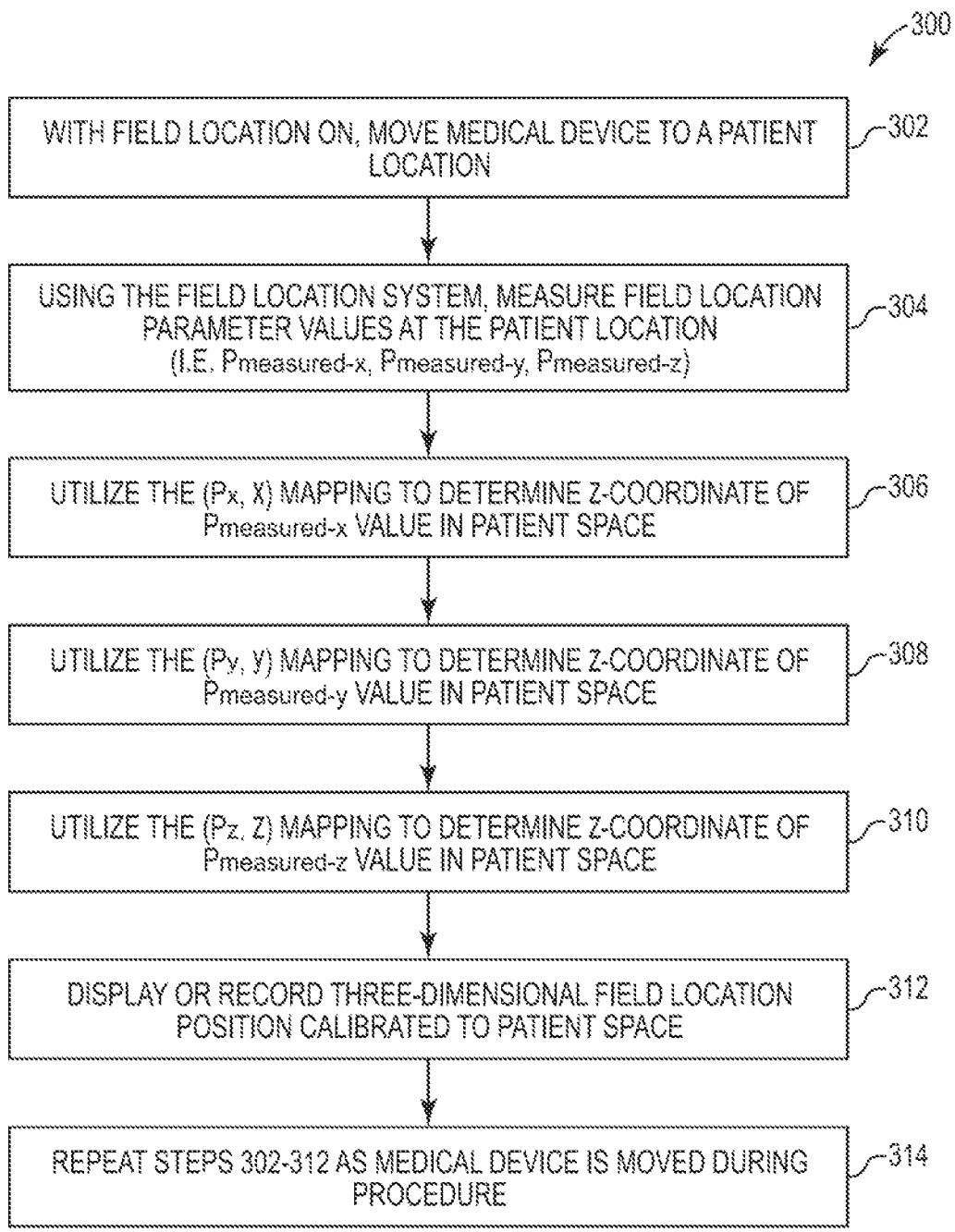
FIG. 8 is a flow diagram illustrating exemplary steps in a locating process in accordance with one embodiment of the present invention.

FIG. 8 is a flow diagram illustrating exemplary steps in the locating process 300 in accordance with one embodiment of the present invention. Beginning in step 302, with the field location system turned on and operational, the medical device may be positioned at or moved to a first patient location within the patient region where calibration was performed. Using the field location system, the field location parameter values at the first patient location are then measured in step 304. The measured field location parameter values include an x-location parameter value ($p_{measured-x}$), a y-location parameter value ($p_{measured-y}$), and a z-location parameter value ($p_{measured-z}$).

Turning next to step 306, the ($p_x$, x) mapping may be utilized to determine an x-coordinate of the measured x-location parameter value in patient space. With reference to FIG. 5, the measured x-location parameter value is first plotted on the field location parameter axis. If the measured x-location parameter value happens to exactly match one of the field location parameter values recorded during the calibration process 200, then the x-coordinate of the measured x-location parameter value in patient space will in turn be the corresponding x-location value calculated during the calibration process. However, because there are an almost infinite number of field location parameter values that could be measured in the patient region of interest, it is unlikely that the measured x-location parameter value will exactly match one of the field location parameter values recorded during the calibration process. In this instance, nearby ($p_x$, x) data points that "surround" the measured x-location parameter value are determined and an interpolation is performed between these ($p_x$, x) data points to calculate an estimated x-coordinate in patient space that corresponds with the measured x-location parameter value in absolute space. This interpolation step may use linear interpolation or any suitable higher order interpolation as will be appreciated by those skilled in the art, such as polynomial interpolation. In the example shown in FIG. 5, the measured x-location parameter value is labeled "$p_{measured-x}$," the closest corresponding data points are ($p_{x5}$, $x_5$) and ($p_{x5}$, $x_6$), and the interpolated x-coordinate is labeled "$X_{interp}$." This interpolated x-coordinate value represents the current patient space location of the medical device in the x-direction.

Turning next to step 308, the ($p_y$, y) mapping may be utilized to determine a y-coordinate of the measured y-location parameter value in patient space. With reference to FIG. 6, the measured y-location parameter value is first plotted on the field location parameter axis. If the measured y-location parameter value happens to exactly match one of the field location parameter values recorded during the calibration process 200, then the y-coordinate of the measured y-location parameter value in patient space will in turn be the corresponding y-location value calculated during the calibration process. However, because there are an almost infinite number of field location parameter values that could be measured in the patient region of interest, it is unlikely that the measured y-location parameter value will exactly match one of the field location parameter values recorded during the calibration process. In this instance, nearby ($p_y$, y) data points that "surround" the measured y-location parameter value are determined and an interpolation is performed between these ($p_y$, y) data points to calculate an estimated y-coordinate in patient space that corresponds with the measured y-location parameter value in absolute space. In the example shown in FIG. 6, the measured y-location parameter value is labeled "$p_{measured-y}$," the closest corresponding data points are ($p_{y3}$, $y_3$) and ($p_{y4}$, $y_4$), and the interpolated y-coordinate is labeled "$y_{interp}$." This interpolated y-coordinate value represents the current patient space location of the medical device in the y-direction.

The process 300 continues with step 310, where the ($p_z$, z) mapping may be utilized to determine a z-coordinate of the measured z-location parameter value in patient space. With reference to FIG. 7, the measured z-location parameter value is first plotted on the field location parameter axis. As discussed above with regard to steps 306 and 308, if the measured z-location parameter value happens to exactly match one of the field location parameter values recorded during the calibration process 200, then the z-coordinate of the measured z-location parameter value in patient space will in turn be the corresponding z-location value calculated during the calibration process. However, it is unlikely that the measured z-location parameter value will exactly match one of the field location parameter values recorded during the calibration process. In this instance, nearby ($p_z$, z) data points that "surround" the measured z-location parameter value are determined and an interpolation is performed between these ($p_z$, z)

data points to calculate an estimated z-coordinate in patient space that corresponds with the measured z-location parameter value in absolute space. In the example shown in FIG. 7, the measured z-location parameter value is labeled "$p_{measured-z}$," the closest corresponding data points are ($p_{z3}$, $z_3$) and ($p_{z4}$, $z_4$), and the interpolated z-coordinate is labeled "$z_{interp}$." This interpolated z-coordinate value represents the current patient space location of the medical device in the z-direction.

Steps 306-310 have been described with reference to calculating the current x-, y-, and z-coordinate values by interpolation merely for purposes of example and not limitation. As will be appreciated by those skilled in the art, the x-, y-, and z-coordinate values may be calculated using any suitable calculation means, such as extrapolation. For example, if the measured x-, y-, or z-location parameter value is outside the range of data points previously recorded, steps 306-310 may alternatively utilize extrapolation to estimate the current coordinate values in patient space. As will be appreciated by those skilled in the art, the extrapolation step may use linear extrapolation or any suitable higher order extrapolation, such as polynomial extrapolation.

As will be appreciated by those skilled in the art, the result of steps 306-310 is a three-dimensional coordinate position that represents the current location of the medical device in patient space that was determined using field location tracking. Once the current location of the medical device in three-dimensional patient space has been determined, the location may be displayed or recorded in any suitable manner as recited in step 312. As will further be appreciated by those skilled in the art, the medical device may be moved or repositioned and the foregoing process repeated to determine the new three-dimensional patient space position as recited in step 314.

Based upon the foregoing discussion, those skilled in the art will appreciate that once a single field location sensor has been calibrated with respect to a single MR tracking coil, the same calibration data sets may be used to determine the positions of additional field location sensors on the device. Thus, when a plurality of field location sensors is present on a device, it is not necessary to provide a corresponding plurality of MR tracking coils.

The calibration process 200 and locating process 300 were described with reference to coordinate sets that include separate ($p_x$, x), ($p_y$, y), and ($p_z$, z) coordinate values "mapped" into three separate mappings as illustrated in FIGS. 5, 6, and 7 merely for purposes of example and not limitation. In one alternative method in accordance with the present invention, a multidimensional coordinate set ($p_{xN}$, xN, $p_{yN}$, yN, $p_{zN}$, zN) may be formed, such as the exemplary coordinate set illustrated in FIG. 9. When a multidimensional coordinate set is generated in the calibration process, each measured parameter value (i.e. $p_{measured-x}$, $p_{measured-y}$, and $p_{measured-z}$) that is measured during the locating process may be interpolated in 3-space using mathematics well known to those skilled in the art to determine the current (x, y, z) location of the medical device in patient space. As will further be appreciated by those skilled in the art, although the mathematics differ when a multidimensional coordinate set is utilized, the general principles of the present invention previously discussed with reference to the calibration process 200 and the locating process 300 are still applicable.

Although several exemplary steps were described with reference to the calibration and locating processes, those skilled in the art will appreciate that the order and number of steps may be modified without departing from the intended scope of the present invention. Thus, the exemplary steps were provided merely for purposes of example and not limitation.

Throughout the disclosure, reference was made to "current" locations, coordinate values, and the like. In this context the term "current" is used to reference a point in time, a point in space, etc., and could be replaced by any synonymous term, such as "present."

As will further be appreciated by those skilled in the art, the processes previously described may be embodied as a system, method, or computer program product. Accordingly, the present invention may take the form of an entirely hardware embodiment, an entirely software embodiment (including firmware, resident software, micro-code, etc.), or an embodiment combining software and hardware aspects that may all generally be referred to as a "circuit," "module," or "system." Furthermore, the present invention may take the form of a computer program product embodied in any tangible medium of expression having computer usable program code embodied in the medium.

The processes comprising the method of the present invention have been described with reference to flow diagrams illustrating exemplary steps. It will be understood that each block of the flowchart diagrams, and combinations of blocks in the flowchart diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart diagram block or blocks.

Although the present invention has been described with reference to preferred embodiments, workers skilled in the art will recognize that changes may be made in form and detail without departing from the spirit and scope of the invention.

What is claimed:

1. A composite tracking system for tracking a medical device, the tracking system configured to be used in an MR environment, comprising:
   an MR compatible field location tracking system including at least one field location sensor structured to be coupled to an outside of the medical device, said medical device movably positioned within a patient;
   a magnetic resonance tracking system including at least one tracking coil structured to be coupled to the outside of the medical device; and
   a processor in electrical communication with the field location tracking system and the magnetic resonance tracking system, the processor operable to (a) receive and process a plurality of positional coordinates from the magnetic resonance tracking system and calculate a plurality of magnetic resonance tracking locations, (b) receive and process a plurality field location parameters from the field location tracking system and determine a plurality of field location parameters that correspond to the plurality of magnetic resonance tracking locations, (c) generate a transfer function for mapping the field location parameters from the field location tracking system to the corresponding positional coordinates of the magnetic resonance tracking system to register the field location coordinate system to the magnetic resonance coordinate system, and (d) determine a present location of the field location sensor by applying the transfer function, wherein said at least one field location sensor and said at least one tracking coil are configured to move relative to the patient.

2. The composite tracking system of claim 1, wherein the field location parameters are selected from voltage, impedence, electrical current, time delay, sound intensity and combinations of the foregoing.

3. The composite tracking system of claim 1 further comprising a plurality of field location sources comprising electrodes operable to create an electric field along three separate axes in three-dimensional space, said field location sources operably coupled to the field location tracking system.

4. The composite tracking system of claim 1, wherein the field location sensor and the tracking coil are separated by a distance less than 5 mm.

* * * * *